United States Patent
Deflorian et al.

(10) Patent No.: US 12,004,629 B2
(45) Date of Patent: Jun. 11, 2024

(54) DIFFUSER OF VOLATILE LIQUID SUBSTANCES EQUIPPED WITH A VAPOR PERMEABLE MEMBRANE, ACTIVATED AT THE TIME OF USE

(71) Applicant: ZOBELE HOLDING S.p.A., Trento (IT)

(72) Inventors: Stefano Deflorian, Trento (IT); Walter Sordo, Trento (IT)

(73) Assignee: ZOBELE HOLDING S.P.A., Trento (IT)

( * ) Notice: Subject to any disclaimer, the term of this patent is extended or adjusted under 35 U.S.C. 154(b) by 0 days.

(21) Appl. No.: 18/256,582

(22) PCT Filed: Dec. 13, 2021

(86) PCT No.: PCT/IB2021/061644
§ 371 (c)(1),
(2) Date: Jun. 8, 2023

(87) PCT Pub. No.: WO2022/130174
PCT Pub. Date: Jun. 23, 2022

(65) Prior Publication Data
US 2023/0389673 A1  Dec. 7, 2023

(30) Foreign Application Priority Data
Dec. 15, 2020  (IT) ................. 102020000030848

(51) Int. Cl.
*A45D 37/00* (2006.01)
*A01M 1/20* (2006.01)
*A61L 9/012* (2006.01)
*A61L 9/12* (2006.01)

(52) U.S. Cl.
CPC ........... *A45D 37/00* (2013.01); *A01M 1/2055* (2013.01); *A61L 9/012* (2013.01); *A61L 9/12* (2013.01); *A45D 2200/1045* (2013.01); *A61L 2209/131* (2013.01); *A61L 2209/134* (2013.01)

(58) Field of Classification Search
CPC .......... A45D 37/00; A45D 2200/1045; A01M 1/2055; A61L 9/012; A61L 9/12; A61L 2209/131; A61L 2209/134
See application file for complete search history.

(56) References Cited

U.S. PATENT DOCUMENTS

| 3,691,090 A | 9/1972 | Kitajima et al. |
| 2003/0168521 A1 | 9/2003 | Skalitzky et al. |
| 2014/0234008 A1 | 8/2014 | Tereschouk |

FOREIGN PATENT DOCUMENTS

| EP | 3257395 A1 | 12/2017 |
| WO | 0103538 A1 | 1/2001 |

OTHER PUBLICATIONS

English language machine translation of Le Joliff WO 0103538 A1 Published Jan. 18, 2001 (Year: 2001).*
International Search Report for PCT/IB2021/061644 dated Apr. 14, 2022, 5 pages.
International Preliminary Report on Patentability for PCT/IB2021/061644 completed Mar. 23, 2023, 6 pages.
Written Opinion of the ISA for PCT/IB2021/061644 dated Apr. 14, 2022, 6 pages.

* cited by examiner

*Primary Examiner* — Alma Pipic
(74) *Attorney, Agent, or Firm* — NIXON & VANDERHYE

(57) ABSTRACT

Disclosed is a diffuser of a volatile liquid substance of the type including a container of the volatile liquid substance, closed by at least one membrane permeable to the vapours of the volatile liquid substance, wherein the container is at least partly flexible and contains a plurality of capsules filled with the volatile liquid substance and made of a pressure-breakable plastic material impermeable to liquid and vapour. The permeable membrane is in direct contact with the external environment.

8 Claims, 2 Drawing Sheets

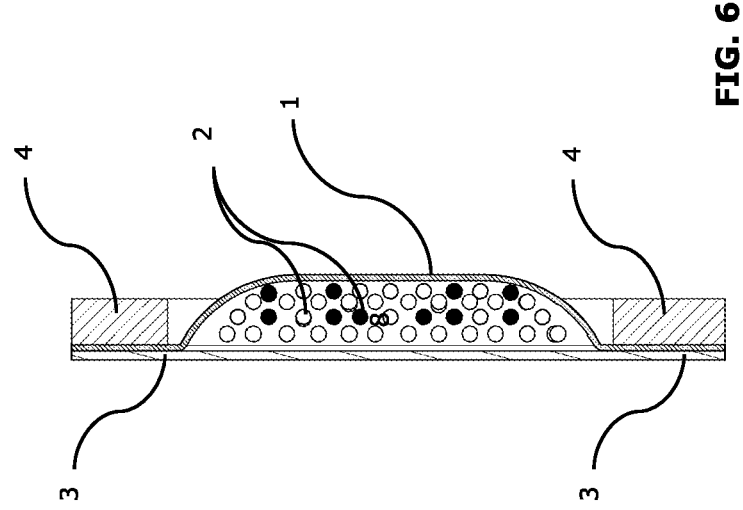
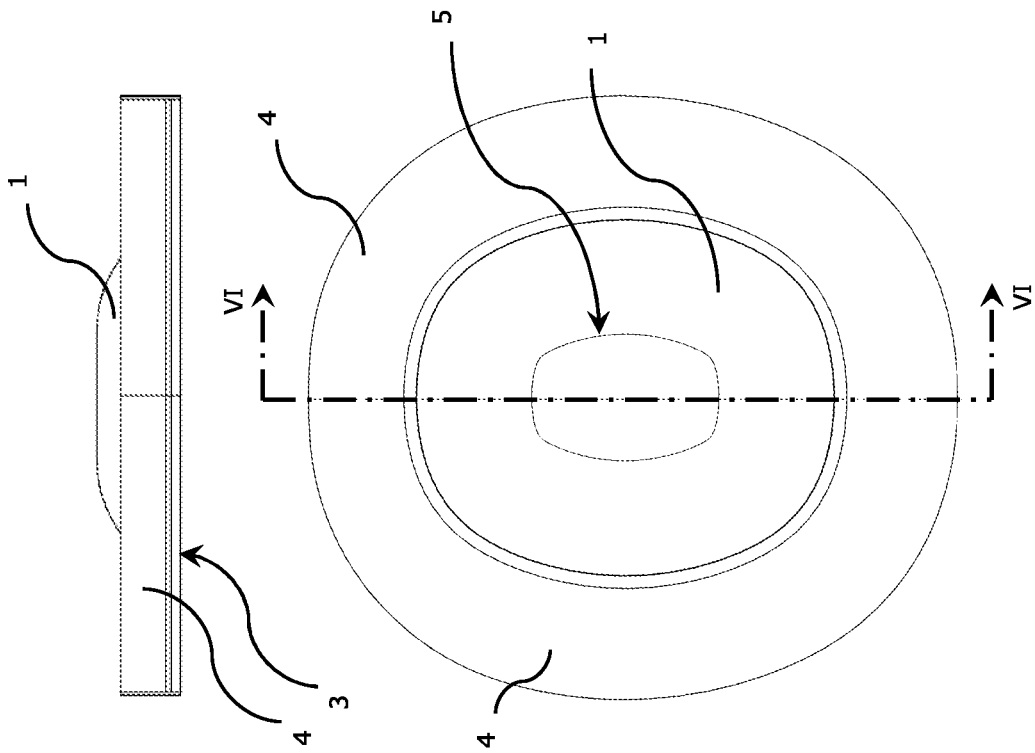

DIFFUSER OF VOLATILE LIQUID SUBSTANCES EQUIPPED WITH A VAPOR PERMEABLE MEMBRANE, ACTIVATED AT THE TIME OF USE

CROSS-REFERENCE TO RELATED APPLICATIONS

This application is the U.S. national phase of International Application No. PCT/IB2021/061644 filed Dec. 13, 2021, which designated the U.S. and claims priority to IT 102020000030848 filed Dec. 15, 2020, the entire contents of each of which are hereby incorporated by reference.

FIELD OF THE INVENTION

The present invention relates to a diffuser of volatile substances with walls at least partly consisting of a vapour permeable membrane, activated at the time of use. More specifically, the invention relates to a diffuser of the type indicated above, preferably having a limited overall bulk and containing a volatile liquid substance which—contrary to what happens with known diffusers of this type—remains inactive until the time of use, without using an external layer of barrier material to protect the vapour permeable membrane.

STATE OF THE PRIOR ART

Widely known on the market are diffusers of volatile liquid substances whose walls are vapour but not liquid permeable membranes, inside which a moderate amount of a volatile liquid, e.g., a perfume, but also a sanitizer, disinfectant or insecticide is placed. Therefore, said diffusers provided with a vapour permeable membrane retain the liquid in their inside, while allowing its vapours to exit and be thus perceived from the outside by the user, without however the liquid wetting or staining its hands or the objects on which the diffuser is placed in use (clothing, handbags, furnishing and the like).

Such diffusers of volatile liquid substances with vapour permeable membrane have rapidly developed and spread on the market due to their simple and economical manufacturing process as well as to their lightness and minimum bulk and their immediate effectiveness and ease of use, which make them perfectly suitable to fulfil their function in all those opportunities of "on-the-go" social life, i.e., those characterized by the need for a pocket-sized response, which is ready to use, efficient and of a relatively short duration.

However, these same diffusers with vapour permeable membrane are not yet completely satisfactory with respect to the needs of a pocket-sized product of this type, since they still imply two important drawbacks. A first drawback is connected to the fact that known diffusers are necessarily marketed complete with a peelable external layer of a barrier material, applied over the permeable membrane to avoid the volatile liquid evaporation during the freight and storage of the product until its first use. Such barrier material, in fact, in addition to cause a complication and an additional cost in the manufacturing phase, becomes a waste that the user must discard after removing it to expose the vapour permeable membrane at the time of activation, thus failing one of the primary features of an on-the-go product, which is the immediacy and ease of use.

A second drawback relates then to the amount of volatile liquid to be placed into said known diffusers. As a matter of fact, if on the one hand the relatively short duration of use of such products, ranging from a few hours to maximum 12 hours, would theoretically require a very small amount of volatile liquid, on the other hand the overall surface of the permeable membrane needs to be relatively wide to obtain a sufficiently intense evaporation, which means that the theoretically necessary moderate amount of volatile liquid would be almost completely absorbed by the permeable membrane and therefore too quickly dispersed at the time of first use. In known diffusers, therefore, volatile liquid is used in excess than that theoretically necessary, leading to much higher production costs. By way of example, whilst in the case of a fine perfume the theoretically necessary amount of volatile liquid could be 300-400 mg, current diffusers are charged 2000-10000 mg of volatile liquid.

The problem addressed by the present invention is therefore that of providing a diffuser of volatile liquid substances which overcomes said drawbacks, i.e., which avoids the use of an external barrier material, and enables the use of a smaller amount of volatile liquid substance, while maintaining the same efficacy of emission of vapours.

Within this problem, a first object of the invention is to use in such a diffuser a type of barrier which preserves the volatile liquid substance from contact with the external environment, without creating a waste to be discarded at the time of use.

A second object of the invention is to provide a diffuser wherein the contact between the volatile liquid substance and the permeable membrane only occurs at the time of use, thus avoiding an early absorption of the volatile liquid substance by the membrane.

SUMMARY OF THE INVENTION

This problem is solved, and these objects achieved by means of a diffuser of volatile liquid substances having the features defined in claim 1. Other preferred features of such diffuser of volatile liquid substances are defined in the secondary claims.

BRIEF DESCRIPTION OF THE DRAWINGS

Further features and advantages of the diffuser of volatile liquid substances of the present invention will anyhow become more evident from the following detailed description of a preferred embodiment of the same, given by mere way of non-limiting example and illustrated in the accompanying drawings, wherein:

FIG. 4 is a side view of the diffuser of FIG. 1;

FIG. 5 is a top view of the diffuser of FIG. 1; and

FIG. 6 is a cross-sectional view of the diffuser of FIG. 1 taken along the line VI-VI of FIG. 5.

DETAILED DESCRIPTION OF THE PREFERRED EMBODIMENT

To solve the problem highlighted above by means of a simple and immediately applicable solution, the diffuser of volatile liquid substances according to the present invention includes first a flexible container 1, having a generally circular or ellipsoidal shape, including a flat annular edge portion 1b and a convex cup-shaped central portion 1c

Figure 3:
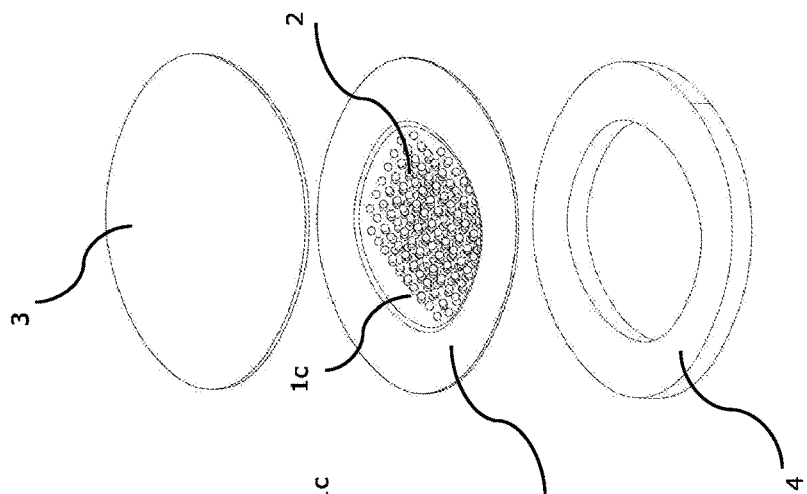
FIG. 3 is an exploded view from below of the diffuser of FIG. 1, illustrating the various component elements.
Figure 2:
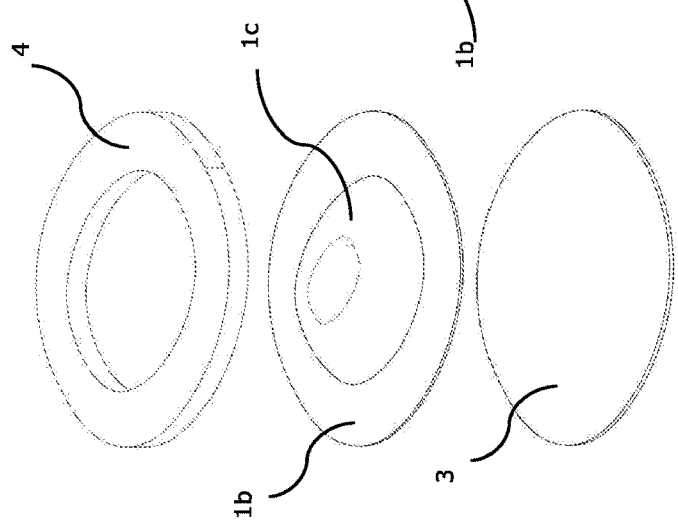
FIG. 2 is an exploded view from above of the diffuser of FIG. 1, illustrating the various component elements.
Figure 1:
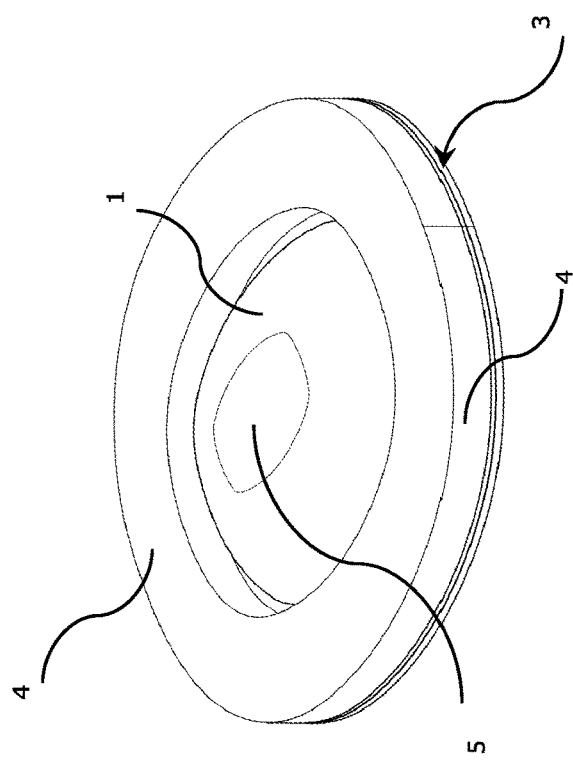
FIG. 1 is a perspective view from above of the diffuser of volatile liquid substances according to the present invention.

(FIGS. 2 and 3). The container 1 is preferably thermoformed starting from a sheet of liquid impermeable plastic material having a reasonably thin thickness to ensure a good compromise between rigidity and flexibility of the cup-shaped central portion 1c. The cup-shaped central portion 1c, in fact, must be sufficiently rigid to maintain its own shape under the normal freight and storage stresses, and flexible enough to be manually crushed by the user due to the reasons that will become clear in the following. The thickness of the container 1 preferably is between 100 and 500 µm.

Between the annular edge portion 1b and the cup-shaped central portion 1c a quite narrow angle is formed, e.g., between and 45°, so that in the step of crushing the cup-shaped central portion 1c against a flat support surface, said cup-shaped central portion 1c can be completely flattened avoiding the formation of cavities at the connection line between the annular edge portion 1b and the cup-shaped central portion 1c.

A plurality of capsules 2 filled with the volatile liquid substance of interest are further arranged inside the cup-shaped central portion 1c of the container 1. The capsules 2 are made of a liquid and vapour impermeable plastic material which material is also frangible, i.e., collapses when subjected to sufficient pressure thus causing the capsules 2 to open and release their volatile liquid substance content. The capsules 2 are generally spherical in shape having a diameter between 1 and 5 mm. The capsules 2 can be arranged loose inside the cup-shaped central portion 1c or alternatively constrained in a predefined arrangement by means of a suitable adhesive. In both cases the overall volume occupied by the capsules 2 is between 20% and 80% of the internal volume of the container 1 wherein the capsules 2 are arranged.

The cup-shaped central portion 1c of the container 1 is closed by a permeable membrane 3, which is vapour permeable and impermeable to liquids. The permeable membrane 3 is preferably flat and bonded to the annular edge portion 1b of the container 1 using a widely known technology. The permeable membrane 3 can be of the so-called monolithic type or, preferably, of the microporous type.

At the time of use, the diffuser is activated by crushing the container 1 between the fingers of one hand or by pressing the container 1, and specifically its cup-shaped central portion 1c, against a flat surface. Optionally, but not preferably, a suitable tool can also be provided to perform said crushing. In this way, the frangible capsules 2 will break and the volatile liquid substance will flow out of them, starting to emit vapours which can freely penetrate the permeable membrane 3 and thus exit the diffuser. As already mentioned above, the shape of the cup-shaped central portion 1c is such as not to give rise to any non-compressible cavity wherein the capsules 2 could get trapped, at the connection area with the annular edge portion 1b. The user can therefore easily and quickly crush all the capsules 2, thereby activating the diffuser without need to remove any barrier layer, and thus without producing any waste to be discarded. As a result, the first object of the invention is fully and effectively achieved.

It is further evident from the above that the second object of the invention is also fully achieved, since the volatile liquid substance remains enclosed within the capsules 2 for the entire period of storage and distribution of the product, getting just partially in contact with the permeable membrane 3 only at the time of use, while a large proportion of the same volatile liquid substance remains adherent to the collapsed capsules 2, from which it then gradually evaporates. So, no early absorption of the volatile liquid substance by the permeable membrane 3 occurs, and therefore not even the typical effect of enhanced emission of vapours in the very first phase of use, which is typical of the known products. The amount of liquid substance contained in the diffuser can thus be conveniently reduced, leading at the same time to both a saving in manufacturing costs and a better and more homogeneous delivery of the vapours of volatile substance from the diffuser over the expected period of operation.

In a preferred embodiment, a flat ring 4 of predefined thickness is arranged around the cup-shaped central portion 1c of the container 1. The flat ring 4 is stably fixed to the annular edge portion 1b of the container 1, completely covering the same, on the side opposite to said permeable membrane 3. In this way the finger of the user is guided in a tactile manner onto the hollow central part of the rigid flat ring 4 and therefore on the cup-shaped central portion 1c, thus facilitating the crushing operation of the capsules 2. The flat ring 4 must be thick enough to be easily perceived in a tactile manner through a user finger, but low enough not to hinder the operation of crushing the cup-shaped central portion 1c containing said capsules 2.

To make even more user-friendly the operation of crushing the cup-shaped central portion 1c of the container 1, a fingerprint 5 or another type of infographic useful to this purpose can be printed on the central part of said portion.

In a further complementary embodiment, the flat ring 4 is rigid and has a self-adhesive external side, covered with a removable non-adhesive sheet. Once the diffuser is activated by crushing the capsules 2, the user can then remove said non-adhesive sheet and attach the diffuser on a support surface by pressing the self-adhesive side of the rigid flat ring 4 against said support surface. It is evident that such embodiment is particularly convenient for a static use inside houses or offices, and not in the on-the-go mode. Therefore, in this case, the presence of the non-adhesive sheet to be discarded as a waste does not entail any drawback.

It is understood, however, that the invention is not to be considered as limited to the specific arrangements illustrated above, which only represent exemplary embodiments thereof, but that different variants are possible, all within the reach of a person skilled in the art, without thereby departing from the scope of protection of the invention, which is solely defined by the following claims.

The invention claimed is:

1. A diffuser of a volatile liquid substance comprising a container of the volatile liquid substance, closed by at least one permeable membrane which is permeable to the vapors of said volatile liquid substance and in direct contact with the external environment, wherein said container is at least partly flexible and contains a plurality of capsules filled with said volatile liquid substance and made of a pressure-breakable plastic material impermeable to liquids and vapors, wherein said container includes an annular edge portion and a cup-shaped central portion containing said plurality of capsules, wherein the angle formed between said annular edge portion and said cup-shaped central portion of the container is between 30° and 45°, the diffuser further comprising a flat ring stably fixed to said annular edge portion of the container.

2. The diffuser of a volatile liquid substance of claim 1, wherein said at least one permeable membrane is flat and bonded to said annular edge portion of the container on the opposite side of said flat ring.

3. The diffuser of a volatile liquid substance of claim 1, wherein said container is made by a thermoforming process, starting from a sheet of plastic material having a thickness of between 100 and 500 μm.

4. The diffuser of a volatile liquid substance of claim 1, wherein capsules of said plurality of capsules are spherical in shape and have a diameter between 1 and 5 mm.

5. The diffuser of a volatile liquid substance of claim 1, wherein the overall volume of said plurality of capsules is between 20% and 80% of the internal volume of the container where said plurality of capsules are housed.

6. The diffuser of a volatile liquid substance of claim 2, wherein said at least one permeable membrane is monolithic or microporous.

7. The diffuser of a volatile liquid substance of claim 2, wherein the thickness of said flat ring is perceivable in a tactile manner by a user finger.

8. The diffuser of a volatile liquid substance of claim 2, wherein said flat ring is rigid and has a self-adhesive external side, covered with a removable non-adhesive sheet, for fixing said diffuser on a support surface.

\* \* \* \* \*